United States Patent [19]

Hiranuma et al.

[11] 4,352,928
[45] Oct. 5, 1982

[54] 5,6-ALKYLENEPYRIMIDINE DERIVATIVE

[75] Inventors: Hidetoshi Hiranuma; Tetsuo Sekiya; Susumu Mizogami; Motokuni Mori; Mitsuo Hanatsuka; Toshiji Kanayama, all of Amimachi, Japan

[73] Assignee: Mitsubishi Yuka Pharmaceutical Co., Ltd., Tokyo, Japan

[21] Appl. No.: 160,080

[22] Filed: Jun. 16, 1980

[30] Foreign Application Priority Data

Jun. 21, 1979 [JP] Japan .................................. 77582/54

[51] Int. Cl.³ .................. C07D 403/04; C07D 405/14; C07D 413/04; A61K 31/505
[52] U.S. Cl. ..................................... 542/431; 544/116; 544/253; 424/251; 424/248.4
[58] Field of Search ................ 544/253, 116; 542/429, 542/405, 431

[56] References Cited

U.S. PATENT DOCUMENTS

| | | | |
|---|---|---|---|
| 3,299,068 | 1/1967 | Chinn | 544/243 |
| 3,635,979 | 1/1972 | Hess | 544/291 |
| 3,757,017 | 9/1973 | Mathieu | 544/253 X |
| 3,925,213 | 1/1976 | Hess | 544/291 |
| 3,980,650 | 9/1976 | Nauta | 544/253 X |

OTHER PUBLICATIONS

McOmie, ed., "Protective Groups in Organic Chemistry," Plenum Press, London & New York (1973).

Primary Examiner—Donald G. Daus
Assistant Examiner—Diana G. Rivers
Attorney, Agent, or Firm—Frishauf, Holtz, Goodman & Woodward

[57] ABSTRACT

There are provided a novel compound, i.e., a 2-piperazino-4-substituted-5,6-alkylenepyrimidine derivative represented by the formula:

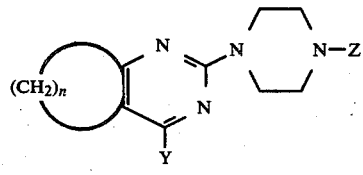

wherein Y, Z and n are defined in the specification and claims, and a pharmaceutically acceptable acid addition salt thereof.

The compounds of the present invention show, an anti-inflammatory effect, a blood sugar level lowering effect, a blood platelet aggregation suppressive effect, an anorexigenic action and a Serotonin effect.

10 Claims, No Drawings

5,6-ALKYLENEPYRIMIDINE DERIVATIVE

The present invention relates to a novel pyrimidine derivative and a process for preparing the same. More particularly, it relates to a 5,6-alkylenepyrimidine derivative which shows, an anti-inflammatory effect, a blood sugar level lowering effect, a blood platelet aggregation suppressive effect, an anorexigenic action and a Serotonin effect, and to a process for preparing the same.

As the 5,6-alkylenepyrimidine derivatives, there has been reported, in *Journal of Chemical Society*, pp. 378 (1946), a compound represented by the following formula:

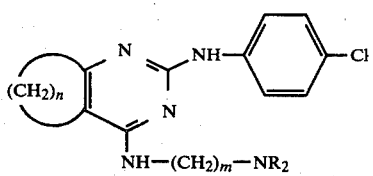

wherein R represents a methyl group or an ethyl group; n represents an integer of 3 or 4; and m represents an integer of 2 or 3,
which compound is useful as an antimaralial agent. In *Journal of Chemical Society*, pp. 3518 (1953), there has been reported 2,4-diamino-5,6-tetramethylenepyrimidine represented by the following formula;

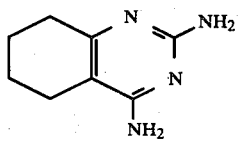

According to Japanese Patent Provisional Publication No. 35-12079/1960, the compound has a carcinostatic effect and an antibacterial activity and, according to Biochem. & Biophys. Res. Commu., 34, 495 (1969), the compound has antagonism against pteridine. In *Journal of Organic Chemisty*, 27, 2708 (1962) and ibid., 30, 1837 (1969), there have been reported 2-methylamino-4-amino-5,6-tetramethylenepyrimidine and 2-dimethylamino-4-amino-5,6-tetramethylenepyrimidine represented by the following formulae:

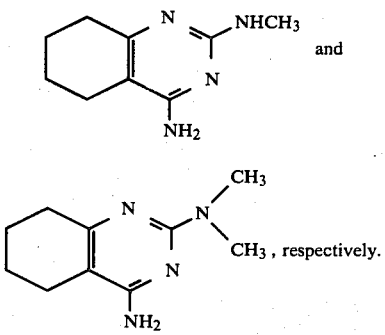

In Collection Czech. Chem. Commu., 29, 2341-5 (1964), there have been reported 2,4-diamino-5,6-tetramethylenepyrimidine derivatives in which at least one amino group are substituted by a chlorophenyl group, as represented by the following formulae:

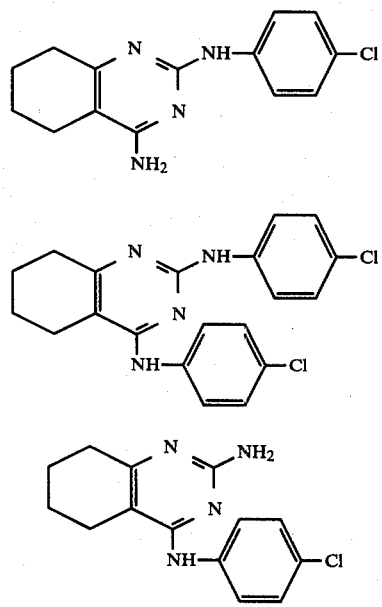

Further, in the specification of British Pat. No. 1152883, there has been disclosed a 5,6-alkylenepyrimidine derivative which may be useful as an anti-hypertensive agent, a peripheral and coronary vasodilator, a diuretic, a bronchiectatic agent, an analgesic anodyne, a circulatory and respiratory stimulant, represented by the following formula:

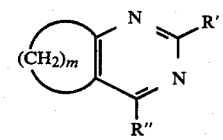

wherein R' and R" each represent a substituent, e.g., a hydroxyalkylamino group and a morpholino group, and m is an integer of 3 to 6.

Further in *Indian Journal of Chemistry*, 9, 202 (1971), there has been reported a 5,6-alkylenepyrimidine derivative which may be useful as a blood sugar level lowering agent, represented by the following formula:

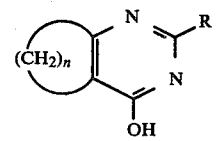

wherein R represents an N-methylpiperazino group, an N-phenylpiperidino group, a 1-piperidino group or a 1-morpholino group; and n represents an integer of 3 to 5.

As a result of the earnest studies upon syntheses and applications of 5,6-alkylenepyrimidine derivatives, the present inventors have succeeded in finding out useful compounds belonging to a 5,6-alkylenepyrimidine derivative which were known heretofore, and then accomplished the present invention.

The primary object of the present invention is to provide a novel 5,6-alkylenepyrimidine derivative which shows, an anti-inflammatory effect, a blood sugar level lowering effect, a blood platelet aggregation suppressive effect, an anorexigenic action and a Serotonin effect.

Another object of the present invention is to provide a new process for preparing the above novel 5,6-alkylnepyrimidine derivative.

Namely, the novel 5,6-alkylenepyrimidine derivative of the present invention is a compound represented by the general formula [I] illustrated as follows, and its pharmaceutically acceptable acid addition salt.

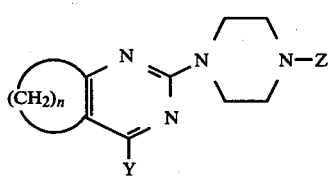

wherein
n represents an integer of 3 to 5;
Y represents a substituted or unsubstituted amino group, and
Z represents a hydrogen atom, a lower alkyl group, a substituted or unsubstituted phenyl group, a substituted or unsubstituted benzyl group, an allyl group, a formyl group, a lower alkylcarbonyl group, a substituted or unsubstituted phenylcarbonyl group, a furoyl group, a thiophenecarbonyl group, a substituted or unsubstituted cinnamoyl group, an acryoyl group, a substituted or unsubstituted furanacryoyl group, a substituted or unsubstituted thiopheneacryoyl group, a lower alkoxycarbonyl group, a lower alkyldithiocarbonyl group, a substituted or unsubstituted benzyldithiocarbonyl group, a lower alkylcarbamoyl group, a substituted or unsubstituted phenylcarbamoyl group, a naphthylcarbamoyl group, a lower alkylthiocarbamoyl group, a substituted or unsubstituted phenylthiocarbamoyl group, a lower alkylsulfonyl group, a substituted or unsubstituted phenylsulfonyl group or a nitrogen-containing aromatic heterocyclic group.

In the above-illustrated formula [I], a substituted amino group represented by Y may be either a monosubstituted or a disubstituted amino group. The substituent may be, for example, a lower alkyl group having 1 to 5 carbon atoms or a lower hydroxyalkyl group having 1 to 5 carbon atoms. The two substituents of a disubstituted amino group may form, together with the nitrogen atom, an alicyclic amino group, such as an aziridino group, a trimethyleneamino group, a pyrrolidino group, a piperidino group and a hexamethyleneamino group, or a morpholino group. The substituted amino groups include a methylamino group, an ethylamino group, a propylamino group, a dimethylamino group, a diethylamino group, a dipropylamino group, a hydroxyethylamino group, a hydroxypropylamino group, a bis(hydroxyethyl)-amino group, a bis(hydroxypropyl)amino group, an ethylmethylamino group and an ethylpropylamino group.

The lower alkyl group represented by Z in formula [I] may preferably be one having 1 to 5 carbon atoms, such as a methyl group, an ethyl group, a propyl group, an isopropyl group, a n-butyl group, a sec-butyl group and a pentyl group.

The substituent in the substituted phenyl group represented by Z may be carried on any carbon atom of the o-, m- and p-positions in the benzene nucleus, and the number of substituents therein may be any of 1 to 3. Examples of the substituent include a lower alkyl group having 1 to 5 carbon atoms, a lower alkoxy group having 1 to 5 carbon atoms, a nitro group and a halogen atom such as chlorine, bromine and iodine. Examples of the substituted phenyl group include an o-methylphenyl group, a m-methylphenyl group, a p-methylphenyl group, an o-methoxyphenyl group, a m-methoxyphenyl group, a p-methoxyphenyl group, an o-nitrophenyl group, a m-nitrophenyl group, a p-nitrophenyl group, an o-chlorophenyl group, a m-chlorophenyl group, a p-chlorophenyl group, a 3,4-dichlorophenyl group, a 2,4-dimethylphenyl group and a 3,4,5-trimetoxyphenyl group.

The substituent in the substituted benzyl group represented by Z may be carried on any carbon atom of the o-, m- and p-positions in the benzene nucleus, and the number of substituents therein may be any of 1 to 3. Examples of the substituent include a lower alkyl group having 1 to 5 carbon atoms, a lower alkoxy group having 1 to 5 carbon atoms, a nitro group and a halogen atom such as chlorine, bromine and iodine. The concrete examples of the substituted benzyl group include an o-methylbenzyl group, a m-methylbenzyl group, a p-methylbenzyl group, an o-methoxybenzyl group, a m-methoxybenzyl group, a p-methoxybenzyl group, an o-nitrobenzyl group, a m-nitrobenzyl group, a p-nitrobenzyl group, an o-chlorobenzyl group, a m-chlorobenzyl group, a p-chlorobenzyl group, a 3,4-dichlorobenzyl group, a 2,4-dimethylbenzyl group and a 3,4,5-trimethoxybenzyl group.

The lower alkylcarbonyl group represented by Z may preferably be one having 2 to 6 carbon atoms, such as an acetyl group, a propionyl group, a butyryl group and a pentanoyl group.

The substituent in the substituted phenylcarbonyl group represented by Z may be carried on any carbon atom of the o-, m- and p-positions in the benzene nucleus, and the number of substituents therein may be any of 1 to 3. Examples of the substituent include a lower alkyl group having 1 to 5 carbon atoms, a lower alkoxy group having 1 to 5 carbon atoms, a nitro group and a halogen atom, such as chlorine, bromine and iodine. Examples of the substituted phenylcarbonyl group include an o-methylphenylcarbonyl group, m-methylphenylcarbonyl group, a p-methylphenylcarbonyl group, an o-methoxyphenylcarbonyl group, a m-methoxyphenylcarbonyl group, a p-methoxyphenylcarbonyl group, an o-nitrophenylcarbonyl group, a m-nitrophenylcarbonyl group, a p-nitrophenylcarbonyl group, an o-chlorophenylcarbonyl group, a m-chlorophenylcarbonyl group, a p-nitrophenylcarbonyl group, a 3,4-dichlorophenylcarbonyl group, a 2,4-dimethylphenylcarbonyl group and a 3,4,5-trimethoxyphenylcarbonyl group.

The substituent in the substituted cinnamoyl group represented by Z may be carried on any carbon atom of the o-, m- and p-positions in the benzene nucleus, and the number of substituents therein may be any of 1 to 3. Examples of the substituent include a lower alkyl group having 1 to 5 carbon atoms, a lower alkoxy group having 1 to 5 carbon atoms, a methylenedioxy group, a nitro group and a halogen atom such as chlorine, bromine and iodine. The concrete examples of the substituted cinnamoyl group include an o-methylcinnamoyl group, a m-methylcinnamoyl group, a p-methylcinnamoyl group, an o-methoxycinnamoyl group, a m-methoxycinnamoyl group, a p-methoxycinnamoyl group, an o-nitrocinnamoyl group, a m-nitrocinnamoyl group, a p-nitrocinnamoyl group, an o-chlorochinnamoyl group, a m-chlorocinnamoyl group, a p-chlorocinnamoyl group, a 3,4-methylenedioxycinnamoyl group, a 3,4-dichlorocinnamoyl group and a 3,4,5-trimethoxycinnamoyl group.

The substituent in the substituted furanacryloyl or thiopheneacryloyl group may be carried on any carbon atom of the 2- to 5-positions in the furan or thiophene ring respectively, and the number of substituents therein may be any of 1 to 3. Examples of the substituent include, a lower alkyl group having 1 to 5 carbon atoms, a nitro group and a halogen atom such as chlorine, bromine and iodine.

Examples of the substituted furanacryoyl group include a 3-(3-methylfuran-2-yl)acryoyl group, a 3-(5-chlorofuran-2-yl)acryoyl group and a 3-(5-nitrofuran-2-yl)acryoyl group. Examples of a thiopheneacryloyl group include a 3-(3-methylthiophen-2-yl)acryoyl group, a 3-(5-chlorothiophen-2-yl)acryoyl group and a 3-(5-nitrothiophen-2-yl)acryoyl.

The lower alkoxycarbonyl group represented by Z may preferably be one having 2 to 6 carbon atoms such as a methoxycarbonyl group, an ethoxycarbonyl group, a n-propoxycarbonyl group, an isopropoxycarbonyl group, a n-butoxycarbonyl group and a pentyloxycarbonyl group.

The lower alkyldithiocarbonyl group represented by Z may preferably be one having 2 to 6 carbon atoms such as a methyldithiocarbonyl group, an ethyldithiocarbonyl group, a n-propyldithiocarbonyl group, a sec-buthyldithiocarbonyl group and a pentyldithiocarbonyl group.

The substituent in the substituted benzyldithiocarbonyl group represented by Z may be carried on any carbon atom of the o-, m- and p-positions in the benzene nucleus, and the number of substituents therein may be any of 1 to 3. Examples of the substituent include a lower alkyl group having 1 to 5 carbon atoms, a lower alkoxy group having 1 to 5 carbon atoms, a nitro group and a halogen atom such as chlorine, bromine and iodine.

Examples of the substituted benzyldithiocarbonyl group include a 2-methylbenzyldithiocarbonyl group, a 3-chlorobenzyldithiocarbonyl group, a 4-methoxydithiocarbonyl group, a 4-nitrobenzyldithiocarbonyl group, a 3,4-dichloromethylbenzylcarbonyl group, a 2,4-dimethylbenzyldithiocarbonyl group and a 3,4,5-trimethoxybenzyldithiocarbonyl group.

The lower alkylcarbamoyl group represented by Z may preferably be one having 2 to 6 carbon atoms such as a methylcarbamoyl group, an ethylcarbamoyl group, a propylcarbamoyl group, a butylcarbamoyl group and a pentylcarbamoyl group.

The substituent in the substituted phenylcarbamoyl group represented by Z may be carried on any carbon atom of the o-, m- and p-positions in the benzene nucleus, and the number of substituents therein may be any of 1 to 3. Examples of the substituent include a lower alkyl group having 1 to 5 carbon atoms, a lower alkoxy group having 1 to 5 carbon atoms, a nitro group and a halogen atom such as chlorine, bromine and iodine.

Examples of the substituted phenylcarbamoyl group include a 2-chlorophenylcarbamoyl group, a 3-chlorophenylcarbamoyl group, a 4-chlorophenylcarbamoyl group, a 2-methylphenylcarbamoyl group, a 4-methoxyphenylcarbamoyl group, a 4-nitrophenylcarbamoyl group, a 3,4-dichlorophenylcarbamoyl group and a 3,4,5-trimethylphenylcarbamoyl group.

The lower alkylthiocarbamoyl group represented by Z may preferably be one having 2 to 6 carbon atoms such as a methylthiocarbamoyl group, an ethylthiocarbamoyl group, a propylthiocarbamoyl group, a butylthiocarbamoyl group and a pentylthiocarbamoyl group.

The substituent in the substituted phenylthiocarbamoyl group represented by Z may be carried on any carbon atom of the o-, m- and p-positions in the benzene nucleus, and the number of substituents therein may be any of 1 to 3. Examples of the substituent include a lower alkyl group having 1 to 5 carbon atoms, a lower alkoxy group having 1 to 5 carbon atoms, a nitro group and a halogen atom such as chlorine, bromine and iodine.

Examples of the substituted phenylthiocarbamoyl group include a 2-methylphenylthiocarbamoyl group, a 3-chlorophenylthiocarbamoyl group, a 4-chlorophenylthiocarbamoyl group, a 4-methoxyphenylthiocarbamoyl group, a 4-nitrophenylthiocarbamoyl group, a 3,4-dichlorophenylthiocarbamoyl group and a 3,4,5-trimethylphenylthiocarbamoyl group.

The lower alkylsulfonyl groups represented by Z may preferably be one having 1 to 5 carbon atoms, such as, a methylsulfonyl group, an ethylsulfonyl group, a propylsulfonyl group, a butylsulfonyl group and a pentylsulfonyl group.

The substituent in the substituted phenylsulfonyl group represented by Z may be carried on any carbon atom of the o-, m- and p-positions in the benzene nucleus, and the number of substituents therein may be any of 1 to 3. The concrete examples of the substituent include a lower alkyl group having 1 to 5 carbon atoms.

Examples of the substituted phenylsulfonyl group include a 2-methylphenylsulfonyl group, a 4-methylphenylsulfonyl group and a 2,4-dimethylphenylsulfonyl group.

As the nitrogen-containing aromatic heterocyclic group, there may be mentioned, for example, a pyridyl group, a quinolyl group a pyrimidinyl group and a quinazolinyl group.

"The pharmaceutically acceptable acid addition salt" means an acid addition salt which does not increase substantially the toxicity of the basic compound.

The acid addition salt according to the present invention includes the salts of mineral acids such as hydrochloric acid, hydroiodic acid, hydrobromic acid, phosphoric acid, methaphosphoric acid, nitric acid and sulfuric acid, and salts of organic acids such as tartaric acid, oxalic acid, benzoic acid, maleic acid, fumaric acid, acetic acid, citric acid, malic acid, gulonic acid, glucuronic acid, succinic acid, an arylsulfonic acid such as p-toluenesulfonic acid and methanesulfonic acid.

1. 2-Piperazino-4-amino-5,6-tetramethylenepyrimidine
2. 2-(4-Methylpiperazino)-4-amino-5,6-tetramethylenepyrimidine
3. 2-(4-Benzylpiperazino)-4-amino-5,6-tetramethylenepyrimidine
4. 2-(4-Allylpiperazino)-4-amino-5,6-tetramethylenepyrimidine
5. 2-(4-Formylpiperazino)-4-amino-5,6-tetramethylenepyrimidine 6. 2-(4-Acetylpiperazine)-4-amino-5,6-tetramethylenepyrimidine
7. 2-(4-Benzoylpiperazino)-4-amino-5,6-tetramethylenepyrimidine
8. 2-(4-Furoylpiperazino)-4-amino-5,6-tetramethylenepyrimidine
9. 2-(4-Acryloylpiperazino)-4-amino-5,6-tetramethylenepyrimidine
10. 2-(4-Cinnamoylpiperazino)-4-amino-5,6-tetramethylenepyrimidine
11. 2-[4-(2-Nitrocinnamoyl)piperazino]-4-amino-5,6-tetramethylenepyrimidine
12. 2-[4-(3,4-Dichlorocinnamoyl)piperazino]-4-amino-5,6-tetramethylenepyrimidine
13. 2-[4-(3,4-Methylenedioxycinnamoyl)piperazino]-4-amino-5,6-tetramethylenepyrimidine
14. 2-[4-{3-(Furan-2-yl)acryloyl}piperazino 2-4-amino-5,6-tetramethylenepyrimidine
15. 2-[4-(3-Thiopheneacryloyl)piperazino]-4-amino-5,6-tetramethylenepyrimidine
16. 2-(4-Isobutoxycarbonylpiperazino)-4-amino-5,6-tetramethylenepyrimidine
17. 2-(Ethylcarbamoylpiperazino)-4-amino-5,6-tetramethylenepyrimidine
18. 2-(4-Phenylcarbamoylpiperazino)-4-amino-5,6-tetramethylenepyrimidine
19. 2-[4-(4-Chlorophenylcarbamoyl)piperazino]-4-amino-5,6-tetramethylenepyrimidine
20. 2-[4-(Methylphenylcarbamoyl)piperazino]-4-amino-5,6-tetramethylenepyrimidine
21. 2-[4-(1-Naphthylcarbamoyl)piperazino]-4-amino-5,6-tetramethylenepyrimidine
22. 2-(Ethylthiocarbamoylpiperazino)-4-amino-5,6-tetramethylenepyrimidine
23. 2-(Phenylthiocarbamoylpiperazino)-4-amino-5,6-tetramethylenepyrimidine
24. 2-(Ethylthiothiocarbonylpiperazino)-4-amino-5,6-tetramethylenepyrimidine
25. 2-(4-Benzylthiothiocarbonylpiperazino)-4-amino-5,6-tetramethylenepyrimidine
26. 2-(4-Methanesulfonylpiperazine)-4-amino-5,6-tetramethylenepyrimidine
27. 2-(4-Tosylpiperazino)-4-amino-5,6-tetramethylenepyrimidine
28. 2-(4-Phenylpiperazino)-4-amino-5,6-tetramethylenepyrimidine
29. 2-[4-(4-Chlorophenyl)piperazino]-4-amino-5,6-tetramethylenepyrimidine
30. 2-[4-(2-Methylphenyl)piperazino]-4-amino-5,6-tetramethylenepyrimidine
31. 2-[4-(4-Methylphenyl)piperazino]-4-amino-5,6-tetramethylenepyrimidine
32. 2-[4-(2-Pyridyl)piperazino]-4-amino-5,6-tetramethylenepyrimidine
33. 2-[4-(2-Quinolyl)piperazino]-4-amino-5,6-tetramethylenepyrimidine
34. 2-(4-Formylpiperazino)-4-methylamino-5,6-tetramethylenepyrimidine
35. 2-Piperazino-4-methylamino-5,6-tetramethylenepyrimidine
36. 2-(4-Formylpiperazino)-4-ethylamino-5,6-tetramethylenepyrimidine
37. 2-Piperazino-4-ethylamino-5,6-tetramethylenepyrimidine
38. 2-(4-Formylpiperazino)-4-butylamino-5,6-tetramethylenepyrimidine
39. 2-Piperazino-4-butylamino-5,6-tetramethylenepyrimidine
40. 2-(4-Formylpiperazino)-4-dimethylamino-5,6-tetramethylenepyrimidine
41. 2-Piperazino-4-dimethylamino-5,6-tetramethylenepyrimidine
42. 2-(4-Formylpiperazino)-4-diethylamino-5,6-tetramethylenepyrimidine
43. 2-Piperazino-4-diethylamino-5,6-tetramethylenepyrimidine
44. 2-(4-Formylpiperazino)-4-pyrrolidino-5,6-tetramethylenepyrimidine
45. 2-Piperazino-4-pyrrolidino-5,6-tetramethylenepyrimidine
46. 2-(4-Methylpiperazino)-4-pyrrolidino-5,6-tetramethylenepyrimidine
47. 2-(4-Formylpiperazino)-4-morpholino-5,6-tetramethylenepyrimidine
48. 2-Piperazino-4-morpholino-5,6-tetramethylenepyrimidine
49. 2-(4-Methylpiperazino)-4-morpholino-5,6-tetramethylenepyrimidine
50. 2-(4-Formylpiperazino)-4-(2-hydroxyethylamino)-5,6-tetramethylenepyrimidine
51. 2-Piperazino-4-(2-hydroxyethyl)amino-5,6-tetramethylenepyrimidine
52. 2-(4-Formylpiperazino)-4-bis(2-hydroxyethyl)amino-5,6-tetramethylenepyrimidine
53. 2-Piperazino-4-bis(2-hydroxyethyl)amino-5,6-tetramethylenepyrimidine
54. 2-Piperazino-4-amino-5,6-trimethylenepyrimidine
55. 2-(4-Formylpiperazino)-4-amino-5,6-trimethylenepyrimidine
56. 2-(4-Benzylpiperazino)-4-amino-5,6-trimethylenepyrimidine
57. 2-(4-Isobutoxycarbonylpiperazino)-4-amino-5,6-trimethylenepyrimidine
58. 2-[4-(3-Furanacryloyl)piperazino]-4-amino-5,6-trimethylenepyrimidine
59. 2-Piperazino-4-methylamino-5,6-trimethylenepyrimidine
60. 2-(4-Formylpiperazino)-4-methylamino-5,6-trimethylenepyrimidine
61. 2-Piperazino-4-morpholino-5,6-trimethylenepyrimidine
62. 2-(4-Formylpiperazino)-4-morpholino-5,6-trimethylenepyrimidine
63. 2-Piperazino-4-amino-5,6-pentamethylenepyrimidine
64. 2-(4-Formylpiperazino)-4-amino-5,6-pentamethylenepyrimidine Next, the process for preparing the compound of the present invention will be described in detail.

The 5,6-alkylenepyrimidine derivative of the formula [I] according to the present invention may be produced according to the following reaction scheme (A).

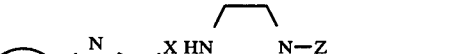

[II]

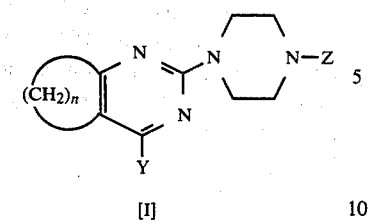

[I]

wherein Y, Z and n are the same as defined above; X represents an easily eliminable group, such as a halogen atom, a lower alkylsulfinyl group and a lower alkylsulfonyl group.

When the substituent X of the starting compound represented by formula [II] is a halogen atom, the compound may be synthesized according to the procesure of Z. Budesinsky et al., namely by the reaction of equimolar amount of a 2,4-dihalogeno derivative [Collection Czechoslo. Chem. Commu. 29, 2341 (1964)] with an amine, represented by Y-H corresponding to the substituent Y. On the other hand, when X is a lower alkylsulfinyl group or a lower alkylsulfonyl group, the compound represented by formula [II] may be prepared by the oxidation of 2-a 2-lower-alkylthiopyrimidine derivative with a suitable oxidizer.

The 2-lower alkylthiopyrimidine derivative may be prepared by the reaction of a cyclic ketone represented by the following formula:

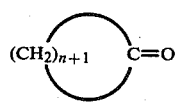

wherein n is an integer of 3 to 5,
with an N-cyano-S-lower-alkylthioisourea (Japanese Patent Provisional Publication No. 89889/1979).

The condensation reaction of the compound represented by the formula [II] and piperazine

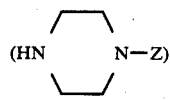

may be carried out without any solvent or in an invert solvent.

As the solvent, there may be employed, for example, an aromatic hydrocarbon such as benzene, toluene and xylene; an ether such as tetrahydrofuran and dioxane; an aliphatic alcohol, such as ethanol, isopropanol and isoamyl alcohol; a ketone, such as acetone or ethylmethyl ketone; an amide such as dimethylacetamide; and dimethylsulfoxide.

The reaction proceeds more smoothly when a base, e.g., an organic base such as triethylamine, N-methylmorpholine, N-dimethylaniline and the like, or an inorganic base such as an alkali metal carbonate, an alkaline earth metal carbonate and the like, or excess amount of pyperazine

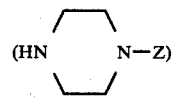

is added to the reaction system.

While the reaction is carried out under heating if necessary, it usually is conducted at a temperatue of 0° to 300° C., preferably, of 100° to 200° C.

The 5,6-alkylenepyrimidine derivative [I] of the present invention may also be prepared according to the following reaction scheme (B).

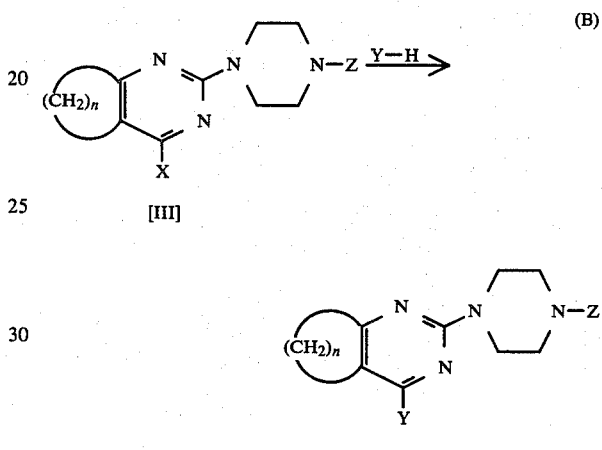

Wherein Y, Z and X are the same as defined above.

In the above reaction scheme (B), when Y—H is an amine, the pyrimidine derivative [I] may be prepared in the same manneras in the reaction of scheme (A).

The reaction is carried out in a solvent. As the solvent, there may be mentioned an inert solvent such as an aromatic hydrocarbon, e.g., benzene, toluene, xylene and the like; and an amide, e.g., dimethylformamide.

The reaction usually is carried out at a temperature of 30° to 250° C., preferably, of 50° to 150° C. The period of time for reaction ranges usually from 10 minutes to 24 hours, preferably, from 30 minutes to 6 hours.

When the piperazino group at the 2-position of the pyrimidine nucleus is not substituted, namely, when the substituent Z is a hydrogen atom in the 5,6-alkylenepyrimidine derivative [I], the compound according to the present invention may also be prepared by the following reaction scheme (C).

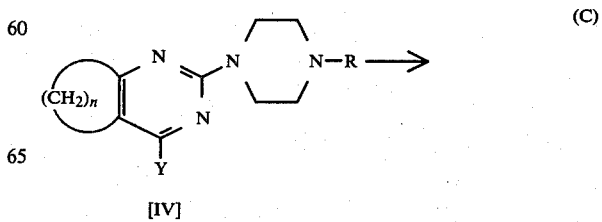

[IV]

-continued

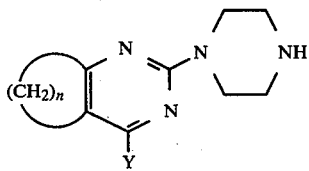

[V]

wherein R represents a protective group, and Y and n have the same meanings as defined above.

The examples of the protective group R in the general formula [IV] include an acyl group, such as formyl group, an acetyl group, a monohalogenoacetyl group, a trihalogenoacetyl group and a substituted or unsubstituted benzoyl group, an aryl group, a substituted or unsubstituted benzyl group, a lower alkoxycarbonyl group and a substituted or unsubstituted benzyloxycarbonyl group. The elimination reaction of the protective group may be carried out in the usual manner as described in "Protective Groups in Organic Chemistry", edited by J. F. M. McOmie, Plenum Press, London & New York (1973).

Moreover, the 5,6-alkylenepyrimidine derivative of the present invention may also be prepared according to the following reaction scheme (D).

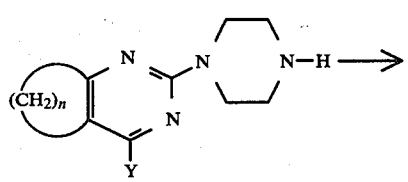

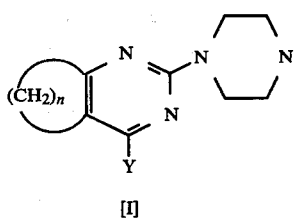

[I]

wherein Y and n have the same meanings as defined above, Z' means the other groups than a hydrogen atom in the groups defined as Z.

The compound [I] of the present invention may be prepared by the condensation or addition reaction of a pyrimidine derivative [V] with an activated derivative of a compound Z'—H, such as, a lower alkyl halide, a substituted or unsubstituted benzyl halide, an acryloyl halide, a lower alkylcarbonyl halide, a substituted or unsubstituted phenylcarbonyl halide, a substituted or unsubstituted cinnamoyl halide, a substituted or unsubstituted acryloyl halide, a lower alkyl isocyanate, a lower alkyl isothiocyanate, a substituted or unsubstituted phenyl isocyanate, a substituted or unsubstituted phenyl isothiocyanate, a lower alkoxycarbonyl halide, a lower alkylsulfonyl halide, a substituted or unsubstituted phenylsulfonyl halide, a pyridyl halide, a quinolyl halide, a pyrimidyl halide, a quinazolyl halide (wherein the halide means chloride, bromide and so on).

This reaction may preferably be carried out with the equimolar amounts of the starting materials, and preferably in an inert solvent. The inert solvent has the same meaning as defined above. The reaction proceeds more smoothly by optional addition of equimolar or excess amount of the base mentioned above. The reaction may be carried out at a temperature of $-30°$ to $250°$ C., preferably, of $0°$ to $150°$ C., and if necessary, under heating.

The reaction period of time usually is 10 minutes to 24 hours, preferably, 30 minutes to 8 hours.

Then, the pharmacological properties of the compounds of the present invention will be described by the following Test Examples.

Test Example 1

Anti-Inflammatory Effect

A Wister male rat having the weight ranging from 120 to 150 g. was starved for 18 hours, and to this was then orally administered the test sample. After lapse of one hour, 0.05 ml. of 1% solution of carrageenan was administered through subcutaneous injection in the plantar surface of the right hind foot to produce inflammation. The volume of the right hind foot was measured prior to the injection of carrageenan and again at 3 hours after the administration through injection. The ratio of the increase of the foot volume was calculated to express in percent based on the measured values. The so calculated ratio was compared with the calculated ratio on the control data to give the dropsical swelling suppressive ratio.

The results are set forth in Table 1.

TABLE 1

| | Anti-Inflammatory Effect | | |
|---|---|---|---|
| Compound No. | Amount of Administration (mg/kg) p.o. | Number of Animals | Suppressive Ratio (%) |
| 3 | 50 | 5 | 46.0 |
| 4 | 50 | 5 | 51.2 |
| 10 | 50 | 3 | 79.9 |
| 14 | 25 | 5 | 53.9 |
| 18 | 50 | 5 | 33.8 |
| 23 | 50 | 5 | 23.9 |
| 28 | 50 | 5 | 52.7 |
| 29 | 50 | 5 | 46.8 |

As seen from the above results, the compounds of the present invention show sufficient anti-inflammatory effects.

Test Example 2

Anti-Hypertensive Effect

To a spontaneously hipertensive rat (SHR), male, aged 20–30 weeks, blood pressure under contraction 150 mmHg. was orally administered the test sample. The mean blood pressure of the rat was measured under non-anesthetic conditions at 1, 3, 6 and 24 hours after the administration via cannula inserted into the main artery in the abdomen.

The results are set forth in Table 2.

TABLE 2

Anti-Hypertensive Effect

| Compound No. | Amount of Administration (mg/kg) p.o. | Number of Animals | Blood Pressure (mmHg.) (Prior to administration of test sample) | Change of Blood Pressure at 3 Hours after Administration (mmHg.) |
| --- | --- | --- | --- | --- |
| 10 | 25 | 4 | 165 | −22 |
| 11 | 50 | 4 | 163 | −17 |
| 18 | 50 | 4 | 174 | −17 |
| 32 | 50 | 4 | 149 | −18 |

As seen from the above results, the compounds of the present invention set forth in Table 2 show anti-hypertensive effects.

Test Example 3

Blood Sugar Level Lowering Effect

To a ICR-JCL mouse, male, having the weight ranging from 25 to 30 g. was orally administered the test sample and, after 15 minutes, 2-deoxy-D-glucose was administered into the cavity of the mouse in the amount of 500 mg/kg to induce a high blood sugar level. The blood was taken after 1 hour, and the blood sugar concentration was determined in the blood serum obtained upon centrifugation, by means of a commercially available test kit (trade name: Glucomesser, produced by Tokyo Zooki Kagaku Co., Ltd., Japan). The results are set forth in Table 3. The suppressive ratio was calculated based on the following equation.

$$R \text{ (Suppressive Ratio)} = \frac{A - C}{A - B} \times 100$$

A: Blood sugar level of the positive control group
B: Blood sugar level of the negative control group
C: Blood sugar level of the test sample administered group

TABLE 3

Blood Sugar Level Lowering Effect

| Sample No. | Amount of Administration (mg/kg) p.o. | Number of Animals | Suppressive Ratio (%) |
| --- | --- | --- | --- |
| 1 | 30 | 7 | 67.8 |
| 14 | 30 | 7 | 60.2 |
| 29 | 10 | 7 | 49.1 |
| 32 | 30 | 7 | 60.1 |
| 35 | 30 | 7 | 77.4 |
| 41 | 30 | 7 | 50.8 |
| 48 | 30 | 7 | 95.9 |
| 54 | 30 | 7 | 106.6 |
| 56 | 30 | 7 | 44.5 |
| 63 | 30 | 7 | 78.9 |

As seen from the above results, the compounds of the present invention show blood sugar level lowering effects.

Test Example 4

Blood Platelet Aggregation Suppressive Effect

A rabbit was starved for 18 hours, and the veinal blood was taken from the carotid artery of the rabbit. The so taken blood and 3.8% sodium citrate solution in the ratio of 1:9 (volume part ratio) were placed in a plastic material made centrifuge tube, and they were well mixed. The mixture was centrifuged at 200 G for 15 minutes to collect the platelet rich plasma (PRP). The residual portion was further centrifuged at 2000 G for 15 minutes to collect the platelet poor plasma (PPP). Subsequently, 250 μl. of the PRP was placed in a cuvette, and the methanol solution containing the test sample of the concentration set forth in Table 4 was added. Incubation was carried out for 2 minutes, and a collagen solution was added to the incubated solution to result in the final concentration of 3 μg./ml. so as to induce aggregation. The condition of the aggregation was measured in the Aggregation Meter (available from Shenco Co., Ltd.) and recorded.

The results are set forth in Table 4. The suppressive ratio was calculated based on the following equation.

$$R \text{ (Suppressive Ratio)} = \frac{A - B}{A} \times 100$$

A: Maximum aggregation ratio observed when a solvent only was added.
B: Maximum aggregation ratio observed when the test sample was added.

TABLE 4

Blood Platelet Aggregation Suppressive Effect

| Compound No. | Concentration (μM) | Suppressive Ratio (%) |
| --- | --- | --- |
| 1 | 100 | 100 |
| 35 | 100 | 87.7 |
| 45 | 30 | 72.0 |
| 46 | 30 | 100 |
| 47 | 30 | 100 |
| 48 | 30 | 46.0 |
| 49 | 30 | 95.2 |
| 51 | 100 | 89.1 |
| Aspirin | 100 | 100 |

As seen from the above results, the compound of the present invention show blood platelet aggregation suppressive effects.

Test Example 5

Acute Toxicity

A ICR-JCL mouse, male, was starved for 18 hours, and to the mouse was orally administered the test sample suspended in 1% tragacantha solution. The condition was observed during one week after the administration and the $LD_{50}$ was calculated.

TABLE 5

Acute Toxicity on Mouse

| Compound No. | Number of Animals | Value $LD_{50}$ (mg/kg) |
| --- | --- | --- |
| 1 | 5 | 750 < |
| 31 | 5 | 400 < |
| 49 | 5 | 500 < |

The present invention is further illustrated by the following Examples and Referential Examples, but these Examples and Referential Examples are not understood to limit the present invention.

Example 1

2-(4-Methylpiperazino)-4-amino-5,6-tetramethylenepyrimidine (Compound No. 2)

To 6 ml. of isoamyl alcohol were added 552 mg. of 2-chloro-4-amino-5,6-tetramethylenepyrimidine and 660 mg. of methylpiperazine, and the mixture was refluxed for 4 hours. After the isoamyl alcohol was removed by distillation under reduced pressure, the residue was dissolved in ethyl acetate and then washed with water. The ethyl acetate layer was dried over anhydrous magnesium sulfate and subsequently the ethyl acetate was removed by distillation. The thus obtained residue was purified by silica gel column chromatography (chloroform: ethyl acetate=4:1) and further treated with hydrochloric acid to give 657 mg. of the hydrochloride of the desired product. Yield: 64.7%.

Melting point (m.p.): 262°–267° C. Elementary Analysis (for $C_{13}H_{21}N_5.2HCl.H_2O$): Found: C; 45.84, H; 7.45, N; 20.70%; Calcd.: C; 46.15, H; 7.45, N; 20.60%.

Examples 2 and 3

2-Substituted amino-4-amino-5,6-tetramethylenepyrimidines

Compounds were synthesized in the same manner as in Example 1, except that methylpiperazine was replaced by corresponding amines.

TABLE 6

| Example No. | Compound No. | amine | Yield (%) | m.p. (°C.) | Elementary analysis: Upper; Found (%) Lower; Calcd. (%) |
|---|---|---|---|---|---|
| 2 | 5 | 4-formyl-piperazine | 64.8 | 197–199 | for $C_{13}H_{19}N_5O$: C; 59.42, H; 7.54, N; 26.69 C; 59.75, H; 7.33, N; 26.80 |
| 3 | 16 | 4-isobutoxy-carbonyl-piperazine | 24.0 | 202–203 | for $C_{17}H_{27}N_5O_2$: C; 61.22, H; 8.30, N; 20.94 C; 61.24, H; 8.16, N; 21.00 |

Example 4

2-(4-Benzylpiperazino)-4-amino-5,6-tetramethylenepyrimidine (Compound No. 3)

(a) In a sealed tube was heated the mixture of 918 mg. of 2-chloro-4-amino-5,6-tetramethylenepyrimidine, 900 mg. of benzylpiperazine, 600 mg. of N-methylmorpholine and 5 ml. of isoamyl alcohol at 180° C. for 5 hours. After cooling, the reaction mixture was concentrated under reduced pressure, and ethyl acetate and water were added to the residue to dissolve it. The thus obtained ethyl acetate layer was dried over anhydrous magnesium sulfate and subsequently concentrated to give an oily substance. The substance was further treated with concentrated hydrochloric acid to give 1.92 g. of the hydrochloride of the desired product. Yield: 90%.

Melting point (m.p.): 283°–285° C. Elementary analysis (for $C_{19}H_{25}N_5.2HCl.H_2O$): Found: C; 55.05, H; 7.07, N; 16.93%; Calcd.: C; 55.07, H; 7.05, N; 16.90%.

(b) Referential Example 1

2-Methylthio-4-amino-5,6-tetramethylenepyrimidine

To 9.8 g. (0.1 mole) of cyclohexanone were added 1.15 g. (0.01 mole) of N-cyano-S-methylisothiourea and 0.06 g. (0.5 millimole) of potassium t-butoxide and the mixture was heated under reflux for 3 hours. After reaction, the excess amount of cyclohexanone was removed by distillation under reduced pressure and 20 ml. of chloroform was added to the residue. Insoluble substances were removed by filtration and the filtrate was purified by silica gel chromatography (eluting solvent: chloroform) to give 1.00 g. of the desired product. Yield: 51.2%.

Melting point (m.p.): 134°–135° C. Elementary analysis (for $C_9H_{13}N_3S$): Found: C; 55.32, H; 6.63, N; 21.72%; Calcd.: C; 55.35, H; 6.71, N; 21.52%.

Referential Example 2

2-Methylsulfonyl-4-amino-5,6-tetramethylenepyrimidine

In 20 ml. of chloroform was dissolved 0.98 g. (5 millimole) of 2-methylthio-4-amino-5,6-tetramethylenepyrimidine obtained in Referential Example 1, and the resulting solution was maintained at a temperature under ice cooling. Then, a solution of 2.88 g. (12 millimole) of 70%-metachloroperbenzoic acid in 40 ml. of chloroform was added dropwise thereto.

After the addition was over, the reaction mixture was allowed to stand at room temperature overnight, and washed sucéesively with 5% aqueous potassium carbonate and with a saturated aqueous sodium chloride. The thus obtained organic layer was dried over anhydrous magnesium sulfate and subsequently concentrated under reduced pressure to give 0.75 g. (3.3 millimole) of a crude product. The crude product was purified by silica gel column chromatography (eluting solvent: chloroform) to give 0.45 g. of the desired product. Yield: 40%. The product was further subjected to recrystallization from isopropanol to afford an analytical sample.

Melting point (m.p.): 195°–196° C. Elementary analysis (for $C_9H_{13}N_3O_2S$): Found: C; 47.68; H; 5.90, N; 18.36, S; 14.00%; Calcd.: C; 47.56, H; 5.76, N; 18.49, S; 14.11%. Infrared absorption (IR) spectrum (cm$^{-1}$): 1605, 1580, 1305 (—$SO_2CH_3$), 1135 (—$SO_2CH_3$).

A mixture of 227 mg. of 2-methylsulfonyl-4-amino-5,6-tetramethylenepyrimidine prepared in Referential Example 2 and 517 mg. of benzylpiperazine was heated at 180° C. for one hour and the resulting reaction mixture was purified by silica gel chromatography (eluting solvent: 1%-ethanol-chloroform) to give an oily product. The product was further treated with concentrated hydrochloric acid to give 496 mg. of the hydrochloride of the desired product. Yield: 93%.

Melting point (m.p.): 283°–285° C.

Example 5

2-(4-Allylpiperazino)-4-amino-5,6-tetramethylenepyrimidine (Compound No. 4)

In a sealed tube were placed 918 mg. of 2-chloro-4-amino-5,6-tetramethylenepyrimidine, 900 mg. of allyl-piperazine, 600 mg. of N-methylmorpholine and 5 ml. of isoamyl alcohol, and the mixture was heated at 180° C. for 5 hours. After cooling, the reaction mixture was concentrated under reduced pressure and then the residue was dissolved by adding water and ethyl acetate thereto. The thus obtained ethyl acetate layer was washed with water and dried over anhydrous magnesium sulfate followed by concentration to give an oily substance. The thus obtained substance was further treated with conc. hydrochloric acid to give the hydrochloride of the desired product. Yield: 59.1%.

Melting point (m.p.): 250°–252° C. Elementary analysis (for $C_{15}H_{23}N_5.2HCl.H_2O$): Found: C; 49.74, H; 7.34, N; 19.23%; Calcd.: C; 49.72, H, 7.46, N; 19.34%.

Examples 6 through 11

2-(4-Substituted piperazino)-4-amino-5,6-tetramethylenepyrimidine

Compounds were synthesized in the same manner as in Example 5, except that the allylpiperazine was replaced by corresponding substituted piperazines respectively.

TABLE 7

| Example No. | Compound No. | Z | Yield (%) | m.p. (°C.) | Elementary analysis: Upper; Found (%) Lower; Calcd. (%) |
|---|---|---|---|---|---|
| 6 | 6 | 4-acetyl | 35.0 | 180–182 | for $C_{14}H_{21}N_5O$: C; 60.91, H; 7.90, N; 25.03 C; 61.06, H; 7.69, N; 25.44 |
| 7 | 7 | 4-benzoyl | 57.6 | 232–234 | for $C_{19}H_{23}N_5O$: C; 67.77, H; 7.03, N; 20.57 C; 67.63, H; 6.87, N; 20.76 |
| 8 | 28 | 4-phenyl | 84.7 | 143–144 | for $C_{18}H_{23}N_5$: C; 69.80, H; 7.64, N; 22.53 C; 69.87, H; 7.49, N; 22.64 |
| 9 | 29 | 4-(4-chlorophenyl) | 62.8 | 152–153 | for $C_{18}H_{22}N_5Cl$: C; 62.57, H; 6.59, N; 22.29 C; 62.87, H; 6.45, N; 22.37 |
| 10 | 30 | 4-(2-methylphenyl) | 46.9 | 155–156 | for $C_{19}H_{25}N_5$: C; 70.49, H; 7.88, N; 21.67 C; 70.55, H; 7.79, N; 21.65 |
| 11 | 31 | 4-(4-methylphenyl) | 51.9 | 118–120 | for $C_{19}H_{25}N_5$: C; 70.43, H; 7.75, N; 21.46 C; 70.55, H; 7.79, N; 21.65 |

Example 12

2-Piperazino-4-amino-5,6-tetramethylenepyrimidine (Compound No. 1)

(a) After 2.61 g. of 2-(4-formylpiperazino)-4-amino-5,6-tetramethylenepyrimidine was heated in 26 ml. of 10% aqueous hydrochloric acid at 100° C. for one hour, the mixture was cooled. The precipitated crystals were collected by filtration and washed with ethanol and subsequently with ether to give 2.82 g. of the hydrochloride of the desired product. Yield: 78.3%.

Melting point (m.p.): melted once at around 200° C. and then solidified, decomposed at over 300° C. Elementary analysis (for $C_{12}H_{19}N_5.2HCl.3H_2O$): Found: C; 39.90, H; 7.34, N; 19.42, Cl; 20.00% Calcd.: C; 40.00, H; 7.56, N; 19.44, Cl; 19.68%

Infrared absorption (IR) spectrum (KBr, $cm^{-1}$): 1670, 1650, 1620.

(b) In 50 ml. of methanol was dissolved 1.61 g. of 2-(4-benzylpiperazino)-4-amino-5,6-tetramethylenepyrimidine and then 0.5 g. of palladium-carbon (10%) was added thereto. The mixture was subjected to catalytic reduction in a stream of hydrogen. After the catalyst was removed by filtration, the methanol was removed by distillation under reduced pressure. Upon addition of 1 ml. of conc. hydrochloric acid to the residue, it crystallized. After filtration, 1.05 g. of the hydrochloride of the desired product was obtained. Yield: 58.7%. The melting point and infrared spectrum of the product were the same as those of the product prepared by Method (a).

Example 13

2-(4-Cinnamoylpiperazino)-4-amino-5,6-tetramethylenepyrimidine (Compound No. 10)

To 20 ml. of tetrahydrofuran were added 0.23 g. of 2-piperazino-4-amino-5,6-tetramethylenepyrimidine, 0.17 g. of cinnamoyl chloride and 0.15 g. of triethylamine. The mixture was stirred at below 10° C. for 1 hour and then allowed to stand at room temperature overnight. After the solvent was removed by distillation under reduced pressure, ethyl acetate and water were added to the residue and the ethyl acetate layer was separated. After washing with water, the ethyl acetate layer was dried over anhydrous magnesium sulfate and then the solvent was removed by distillation. Upon addition of ether to the residue, it crystallized. The thus obtained crystals were collected by filtration to give 0.19 g. of the desired product. Yield: 51%.

Melting point (m.p.): 258°–260° C. Mass spectrum (m/e): 363 (M+), 177.

Example 14

2-[4-{3-(Furan-2-yl)acryloyl}piperazino]-4-amino-5,6-tetramethylenepyrimidine (Compound No. 14)

To 30 ml. of ethyl acetate were added 83 mg. of furanacrylic acid, 65 mg. of ethyl chlorocarbonate and 250 mg. of triethylamine. The mixture was stirred at below 5° C. for 30 min. After 180 mg. of 2-piperazino-4-amino-5,6-tetramethylenepyrimidine hydrochloride was added thereto, the mixture was stirred at room temperature overnight. To the reaction mixture were added water and ethyl acetate, and the ethyl acetate layer was separated. The ethyl acetate layer was washed with water and dried over anhydrous magnesium sulfate, followed by removal of the solvent by distillation under reduced pressure. Upon addition of ether to the residue, it crystallized. The thus obtained crystals were collected by filtration to give 84 mg. of the desired product. Yield: 62%.

Melting point (m.p.): 197°–198° C. Elementary analysis (for $C_{19}H_{23}N_5O_2$): Found: C; 64.44, H; 6.56, N; 19.90%; Calcd.: C; 64.57, H; 6.56, N; 19.82%.

Examples 15 through 20

2-(4-Substituted piperazino)-4-amino-5-6-tetramethylenepyrimidine

Compounds were synthesized in the same manner as in Example 14, except that furanacrylic acid was replaced by corresponding carboxylic acid derivatives.

TABLE 8

| Example No. | Compound No. | Z | Yield (%) | m.p. (°C.) | IR spectrum (cm$^{-1}$) |
|---|---|---|---|---|---|
| 15 | 15 | 3-thiophene-acryloyl | 30 | 182–183 | 1640, 1585 |
| 16 | 11 | 2-nitro-cinnamoyl | 51 | 218–220 | 1640, 1620, 1600 |
| 17 | 12 | 3,4-dichloro-cinnamoyl | 60 | 219–221 | 1645, 1600 |
| 18 | 13 | 3,4-methyl-enedioxy-cinnamoyl | 44 | 200–221 | 1640, 1620, 1600 |
| 19 | 9 | acryloyl | 20 | 184–186 | 1640, 1610, 1580 |
| 20 | 8 | furoyl | 50 | 211–214 | 1610, 1585 |

Example 21

2-(4-Phenylcarbamoylpiperizino)-4-amino-5,6-tetramethylenepyrimidine (Compound No. 18)

To 5 ml. of tetrahydrofuran were added 0.36 g. of 2-piperazino-4-amino-5,6-tetramethylenepyrimidine hydrochloride and 0.35 g. of triethylamine. To the resulting mixture was added dropwise 0.12 g. of phenyl isocyanate under ice cooling. The mixture was stirred for one hour and then water and ethyl acetate were added thereto. The ethyl acetate layer was separated and washed with water. After the ethyl acetate layer was dried over anhydrous magnesium sulfate, the ethyl acetate was removed by distillation under reduced pressure. To the thus obtained residue was added 10% aqueous hydrochloric acid and the mixture was subjected to recrystallization in ethanol to give 0.286 g. of the hydrochloride of the desired product. Yield: 67.3%.

Melting point (m.p.): 255° C. (decomposed). Mass spectrum (m/e): 352 (M+), 177, 119.

Examples 22 through 27

2-[4-(N-Substituted carbamoyl) piperazino]-4-amino-5,6-tetramethylenepyrimidines Compounds were synthesized in the same manner as in Example 21, except that phenyl isocyanate was replaced by corresponding isocyanates.

TABLE 9

| Example No. | Compound No. | Z | Yield (%) | m.p. (°C.) | Mass spectrum (m/e) |
|---|---|---|---|---|---|
| 22 | 17 | ethylcarbamoyl | 80 | 176–178 | 304 (M+), 177 |
| 23 | 19 | 4-chlorophenylcarbamoyl | 46 | 192–194 | 386 (M+), 153 |
| 24 | 20 | 2-methylphenylcarbamoyl | 32 | 190–200 (hydrochloride) | 366 (M+), 133 |
| 25 | 21 | 1-naphthylcarbamoyl | 61 | 124–126 | 422 (M−), 169 |
| 26 | 22 | ethylthiocarbamoyl | 75 | 211–216 (hydrochloride) | 320 (M+), 177 |
| 27 | 23 | phenylthiocarbamoyl | 86 | 194–195 | 368 (M+), 135 |

Example 28

2-(4-Ethylthiothiocarbonylpiperazino)-4-amino-5,6-tetramethylenepyrimidine (Compound No. 24)

To the mixed solvent of 10 ml. of water and 10 ml. of ethanol were added 720 mg. of 2-piperazino-4-amino-5,6-tetramethylenepyrimidine hydrochloride, 228 mg. of carbon disulfide and 264 mg. of sodium hydroxide. The resulting mixture was stirred under ice cooling for two hours. After 361 mg. of ethyl iodide (95%) was added thereto, the reaction mixture was heated under reflux for 4 hours. The crystals precipitated in the aqueous layer were collected by filtration. The thus obtained crystals were subjected to recrystallization from methanol to give 400 mg. of the desired product. Yield: 59.2%.

Melting point (m.p.): 167°–169° C. Elementary analysis (for $C_{15}H_{23}N_5S_2$): Found: C; 53.45, H; 7.15, N; 20.75% Calcd.: C; 53.38, H; 6.87, N; 20.75%

Example 29

2-(4-Benzylthiothiocarbonylpiperazino)-4-amino-5,6-tetramethylenepyrimidine (Compound No. 25)

The compound was synthesized in the same manner as in Example 28, except that ethyl iodide was replaced by benzyl chloride. Yield: 60.6%.

Melting point (m.p.): 119°–121° C. Elementary analysis (for $C_{20}H_{25}N_5S_2$): Found: C; 59.97, H; 6.32, N; 17.63%; Calcd.: C; 60.12, H; 6.31, N; 17.53%.

Example 30

2-(4-Methanesulfonylpiperazino)-4-amino-5,6-tetramethylenepyrimidine (Compound No. 26)

To 10 ml. of tetrahydrofuran were added 720 mg. of 2-piperazino-4-amino-5,6-tetramethylenepyrimidine hydrochloride, 252 mg. of methanesulfonyl chloride and 909 mg. of triethylamine under ice cooling. After stirring at room temperature for 6 hours, water and chloroform were added thereto and then the chloroform layer was separated. After washing with water, the chloroform layer was dried over anhydrous magnesium sulfate and subsequently the solvent was removed by distillation under reduced pressure. The thus obtained residue was subjected to crystallization in a mixture of benzene and ether to give 170 mg. of the desired product. Yield: 27.3%.

Melting point (m.p): 201°–203° C. Mass spectrum (m/e): 311 (M+), 232

Example 31

2-(4-Paratoluenesulfonylpiperazino)-4-amino-5,6-tetramethylenepyrimidine (Compound No. 27)

The compound was synthesized in the same manner as in Example 30, except that methanesulfonyl chloride was replaced by paratoluenesulfonyl chloride. Yield: 78.3%.

Melting point (m.p.): 181°–182° C. Elementary analysis (for $C_{19}H_{25}N_5SO_2$): Found: C; 58.82, H; 6.68, N;

18.09, S; 8.20%; Calcd.: C; 58.89, H; 6.50, N; 18.07, S; 8.27%.

Example 32

2-{4-(Pyridin-2-yl)-piperazino}-4-amino-5,6-tetramethylenepyrimidine (Compound No. 32)

To 5 ml. of isoamyl alcohol placed in a sealed tube were added 0.50 g. of 2-chloro-4-amino-5,6-tetramethylenepyrimidine and 0.53 g. of 2-piperazino-pyridine, and the mixture was heated at 180° C. for six and a half hours and then the isoamyl alcohol was removed by distillation under reduced pressure. After neutralization, the residue was dissolved by adding ethyl acetate and water thereto. The thus obtained ethyl acetate layer was washed with water and dried over anhydrous magnesium sulfate and then the ethyl acetate was removed by distillation to give 0.80 g. of an oily product. Yield: 95%. The product was further subjected to crystallization to give the hydrochloride of the product.

Melting point (m.p.): 172°–175° C. Mass spectrum (m/e): 310 (M+), 177

Example 33

2-{4-(Quinolin-2-yl)piperazino}-4-amino-5,6-tetramethylenepyrimidine (Compound No. 33)

To 20 ml. of isoamyl alcohol placed in a sealed tube were added 467 mg. of 2-piperazino-4-amino-5,6-tetramethylenepyrimidine and 327 mg. of 2-chloro quinoline, and the mixture was heated at 180° C. for 8 hours. After the isoamyl alcohol was removed by distillation, 10% aqueous potassium carbonate and ethyl acetate were added to the residue. The ethyl acetate layer was separated and dried over magnesium sulfate, and subsequently the ethyl acetate was removed by distillation. The thus obtained residue was purified by column chromatography (silica gel, chloroform: methanol=99:1) to give 470 mg. of the desired product. Yield: 65.2%.

Melting point (m.p.): 267°–275° C. (as hydrochloride). Mass spectrum (m/e): 360 (M+), 177.

Referential Example 3

2-Chloro-4-methylamino-5,6-tetramethylenepyrimidine

After 2.03 g. of 2,4-dichloro-5,6-tetramethylenepyrimidine was dissolved in 10 ml. of tetrahydrofuran and 1.71 g. of 40% aqueous solution of methylamine was added dropwise thereto under ice cooling, the mixture was allowed to stand at room temperature overnight. After water and chloroform were added thereto and the mixture was stirred sufficiently, chloroform layer was separated and dried over magnesium sulfate. Subsequently the chloroform was removed by distillation under reduced pressure. The thus obtained residue was recrystallized from ethyl acetate to give 1.14 g. of the desired product. Yield: 57.6%.

Melting point (m.p.): 204°–205° C. Elementary analysis (for $C_9H_{12}N_3Cl$): Found: C; 54.65, H; 6.23, N; 21.39% Calcd.: C; 54.68, H; 6.12, N; 21.26%

Referential Examples 4 through 11

2-Chloro-4-substituted amino-5,6-tetramethylenepyrimidines

The following compounds of 2-chloro-4-substituted amino-5,6-tetramethylenepyrimidines were synthesized in the same manner as in Referential Example 3, except that the 40% aqueous solution of methylamine was replaced by corresponding amines.

TABLE 10

| Referential No. | Y | m.p. (°C.) |
|---|---|---|
| 4 | ethylamino | 127–128 |
| 5 | butylamino | 78–79 |
| 6 | dimethylamino | 77–79 |
| 7 | diethylamino | 32–33 |
| 8 | pyrrolidino | 106–107 |
| 9 | morpholino | 183–184 |
| 10 | 2-hydroxyethylamino | 141–142 |
| 11 | bis(2-hydroxyethyl)amino | 93–98 |

Example 34

2-(4-Formylpiperazino)-4-methylamino-5,6-tetramethylenepyrimidine (Compound No. 34)

To 20 ml. of isoamyl alcohol were added 1.98 g. of 2-chloro-4-methylamino-5,6-tetramethylenepyrimidine and 2.36 g. of formylpiperazine, and the mixture was refluxed for 4 hours. After the isoamyl alsohol was removed by distillation, the residue was stirred thoroughly after addition of chloroform and water. The chloroform layer was separated and dried over magnesium sulfate, and then the chloroform was removed by distillation. The thus obtained residue was recrystallized from ethyl acetate to give 1.26 g. of the desired product.

Melting point (m.p.): 75°–77° C. Elementary analysis (for $C_{14}H_{21}N_5O$): Found: C; 60.97, H; 7.80, N; 25.74% Calcd.: C; 61.07, H; 7.69, N; 25.44%

Examples 35 through 44

2-(4-Substituted piperazino)-4-substituted amino-5,6-tetramethylenepyrimidines

The following compounds of 5,6-tetramethylenepyrimidine derivatives were synthesized in the same manner as in Example 34, except that the 2-chloro-4-methylamino-5,6-tetramethylenepyrimidine was replaced by corresponding 2-chloro-4-substituted amino-5,6-tetramethylenepyrimidines.

TABLE 11

| Example No. | Compound No. | Z | Y | Yield (%) | m.p. (°C.) | Mass spectrum (m/e) | IR spectrum (cm$^{-1}$) |
|---|---|---|---|---|---|---|---|
| 35 | 36 | formyl | ethylamino | 72.5 | oil | 289 (M+), 205 | 1670, 1580, 1560 |
| 36 | 38 | for,myl | butylamino | 60.0 | 130–132 | 317 (M+), 233 | — |
| 37 | 40 | formyl | diemthylamino | 66.8 | oil | 289 (M+), 205 | 1675, 1575, 1550 |
| 38 | 42 | formyl | dimethylamino | 67.3 | oil | 317 (M+), 233 | 1670, 1580, 1550 |
| 39 | 44 | formyl | pyrrolidino | 43.7 | 151–153 | 315 (M+), 231 | — |
| 40 | 46 | methyl | pyrrolidino | 43.3 | 163–164 hydro- | 301 (M+), 231 | — |

TABLE 11-continued

| Example No. | Compound No. | Z | Y | Yield (%) | m.p. (°C.) | Mass spectrum (m/e) | IR spectrum (cm$^{-1}$) |
|---|---|---|---|---|---|---|---|
| | | | | | chloride) | | |
| 41 | 47 | formyl | morpholino | 43.3 | 149–151 | 331 (M$^+$), 247 | — |
| 42 | 49 | methyl | morpholino | 78.0 | oil | 317 (M$^+$), 247 | 1560, 1540 |
| 43 | 50 | formyl | 2-hydroxy-ethylamino | 53.7 | 158–160 | 305 (M$^+$), 221 | — |
| 44 | 52 | formyl | bis(2-hydroxy-ethyl)amino | 66.8 | oil | 349 (M$^+$), 265 | 1670, 1580 |

Example 45

2-Piperazino-4-methylamino-5,6-tetramethylenepyrimidine (Compound No. 35)

To 10 ml. of 10% aqueous solution of hydrochloric acid was added 550 mg. of 2-(4-formylpiperazino)-4-methylamino-5,6-tetramethylenepyrimidine, and the mixture was heated at 100° C. for one hour. After cooling, the mixture was neutralized by adding 10% aqueous potassium carbonate and then extracted with ethyl acetate. After the organic layer was dried over magnesium sulfate, the ethyl acetate was removed by distillation to give 450 mg. of the desired product. Yield: 91.1%.

Melting point (m.p.): 129°–130° C. Elementary analysis (for C$_{13}$H$_{21}$N$_5$): Found: C; 62.95, H; 8.76, N; 28.27%; Calcd.: C; 63.13, H; 8.56, N; 28.32%.

Examples 46 through 53

2-Piperazino-4-substituted amino-5,6-tetramethylenepyrimidines

The following 2-piperazino-4-substituted amino-5,6-tetramethylenepyrimidine compounds were synthesized in the same manner as in Example 45, except that 2-(4-formylpiperazino)-4-methylamino-5,6-tetramethylenepyrimidine was replaced by corresponding 2-(4-formylpiperazino-4-substituted amino-5,6-tetramethylenepyrimidines.

sulfate. Subsequently the ethyl acetate was removed by distillation to give 2.40 g. of the desired product. Yield: 53%.

Melting point (m.p.): 243°–245° C. Mass spectrum (m/e): 247 (M$^+$), 163.

Example 55

2-Piperazino-4-amino-5,6-trimethylenepyrimidine (Compound No. 54)

To 7 ml. of 10% aqueous solution of hydrochloric acid was added 720 mg. of 2-(4-formylpiperazino)-4-amino-5,6-trimethylenepyrimidine and the mixture was heated under reflux for one hour. Upon cooling, it crystallized. The thus obtained crystals were collected by filtration to give 450 mg. of the hydrochloride of the desired product. Yield: 49.4%.

Melting point (m.p.): 273°–275° C. (dehydrated at 168°–178° C.) Mass spectrum (m/e): 219 (M$^+$), 163.

Example 56

2-(4-Benzylpiperazino)-4-amino-5,6-trimethylenepyrimidine (Compound No. 56)

To 5 ml. of isoamyl alcohol placed in a sealed tube were added 0.857 g. of 2-chloro-4-amino-5,6-trimethylenepyrimidine, 1.80 g. of N-benzylpiperazine, 1.29 g. of triethylamine and the mixture was heated at 180° C. for 5 hours. The reaction mixture was further treated in the same manner as in Example 7 to give 1.23 g. of the

TABLE 12

| Example No. | Compound No. | Y | Yield (%) | m.p. (°C.) | Mass spectrum (m/e) | IR spectrum (cm$^{-1}$) |
|---|---|---|---|---|---|---|
| 46 | 37 | ethylamino | 46.9 | 111–114 | 261 (M$^+$), 205 | — |
| 47 | 39 | butylamino | 63.0 | 225–227 (picrate) | 289 (M$^+$), 233 | — |
| 48 | 41 | dimethylamino | 73.5 | 175–178 (oxalate) | 261 (M$^+$), 205 | 1570, 1550 |
| 49 | 43 | diethylamino | 87.5 | 47–48 | 289 (M$^+$), 233 | — |
| 50 | 45 | pyrrolidino | 62.5 | 136–137 | 297 (M$^+$), 241 | — |
| 51 | 48 | morpholino | 36.4 | 115–117 | 303 (M$^+$), 247 | — |
| 52 | 51 | 2-hydroxy-ethylamino | 54.7 | 209–211 (picrate) | 277 (M$^+$), 221 | — |
| 53 | 53 | bis(2-hydroxy-ethyl)amino | 40.8 | 105–115 (decomposed, picrate) | 321 (M$^+$), 265 | — |

Example 54

2-(4-Formylpiperazino)-4-amino-5,6-trimethylenepyrimidine (Compound No. 55)

To 20 ml. of isoamyl alcohol were added 3.44 g. of 2-chloro-4-amino-5,6-trimethylenepyrimidine (melting point, 247°–249° C.), 2.80 g. of N-formylpiperazine and 2.20 g. of triethylamine. The mixture was heated under reflux for 5 hours and subsequently the isoamyl alcohol was removed by distillation under reduced pressure. After the residue was extracted by adding water and ethyl acetate, the organic layer was separated, followed by washing with water and drying over magnesium hydrochloride of the desired product. Yield: 60%.

Melting point (m.p.): 195°–198° C. Elementary analysis (for C$_{18}$H$_{23}$N$_5$.2HCl.H$_2$O): Found: C; 54.27, H; 6.54, N; 17.53%; Calcd.: C; 54.27, H; 6.78, N; 17.59%.

Example 57

2-(4-Isobutoxycarbonylpiperazino)-4-amino-5,6-trimethylenepyrimidine (Compound No. 57)

The desired product was obtained in the same manner as in Example 56, except that N-benzylpiperazine was replaced by isobutoxycarbonylpiperazine. Yield: 24%.

Melting point (m.p.): 208°–209° C. Mass spectrum (m/e): 319 (M+), 163

Example 58

2-[4-(3-Furanacryloyl)piperazino]-4-amino-5,6-trimethylenepyrimidine (Compound No. 58)

The desired product was obtained in the same manner as in Example 56, except that N-benzylpiperazine was replaced by 3-furanacryloylpiperazine. Yield: 58%.

Melting point (m.p.): 204°–205° C. Mass spectrum (m/e): 339 (M+), 163.

Example 59

2-(4-Formylpiperazino)-4-amino-5,6-pentamethylenepyrimidine (Compound No. 64)

To 10 ml. of isoamyl alcohol were added 792 mg. of 2-chloro-4-amino-5,6-pentamethylenepyrimidine (melting point; 217°–218° C.) and 1.15 g. of N-formylpyrimidine, and the mixture was heated under reflux for 4 hours. After the isoamyl alcohol was removed by distillation, chloroform and water were added to the residue. After the chloroform layer was separated and dried over magnesium sulfate, the chloroform was removed by distillation. The thus obtained residue was purified by column chromatography (silica gel, 1% ethanol-chloroform) to give 0.32 g. of the desired product. Yield: 32.7%.

Melting point (m.p.): 172°–173° C. Elementary analysis (for $C_{14}H_{21}N_5O$): Found: C; 61.14, H; 7.77, N; 25.72%; Calcd.: C; 61.07, H; 7.69, N; 25.44%.

Example 60

2-Piperazino-4-amino-5,6-pentamethylenepyrimidine (Compound No. 63)

To 7 ml. of 10% aqueous solution of hydrochloric acid was added 180 mg. of 2-(4-formylpiperazino)-4-amino-5,6-pentamethylenepyrimidine, and the mixture was heated under reflux for 4 hours. The reaction mixture was neutralized by addition of 10% aqueous sodium hydroxide and extracted with chloroform. After the chloroform layer was separated and dried over magnesium sulfate, the chloroform was removed by distillation to give 127 mg. of the desired product. Yield: 79%.

Melting point (m.p.): 145°–146° C. Elementary analysis (for $C_{13}H_{21}N_5$): Found: C; 63.08, H; 8.68, N; 28.32%; Calcd.: C; 63.12, H; 8.56, N; 28.32%.

Example 61

2-(4-Formylpiperazino)-4-methylamino-5,6-trimethylenepyrimidine (Compound No. 60)

The desired product was obtained in the same manner as in Example 34, except that 2-chloro-4-methylamino-5,6-tetramethylenepyrimidine was replaced by 2-chloro-4-methylamino-5,6-trimethylenepyrimidine (melting point; 194°–195° C.) Yield: 62.3%.

Melting point (m.p.): 188°–190° C. Mass spectrum (m/e): 261 (M+), 177.

Example 62

2-(4-formylpiperazino)-4-morpholino-5,6-trimethylenepyrimidine (Compound No. 62)

The desired product was obtained in the same manner as in Example 34, except that 2-chloro-4-methylamino-5,6-tetramethylenepyrimidine was replaced by 2-chloro-4-morpholino-5,6-trimethylenepyrimidine (melting point; 113°–114° C.) Yield: 41.2%.

Melting point (m.p.): 157°–160° C. Mass spectrum (m/e): 317 (M+), 233

Example 63

2-Piperazino-4-methylamino-5,6-trimethylenepyrimidine (Compound No. 59)

The desired product was obtained in the same manner as in Example 45, except that 2-(4-formylpiperazino)-4-methylamino-5,6-trimethylenepyrimidine was replaced by 2-(4-formylpiperazino)-4-methylamino-5,6-tetramethylenepyrimidine. Yield: 86.8%.

Melting point (m.p.): 192°–194° C. Mass spectrum (m/e): 233 (M+), 177.

Example 64

2-Piperazino-4-morpholino-5,6-trimethylenepyrimidine (Compound No. 61)

The desired product was obtained in the same manner as in Example 45, except that the 2-(4-formylpiperazino)-4-methylamino-5,6-tetramethylenepyrimidine was replaced by 2-(4-formylpiperazino)-4-morpholino-5,6-trimethylenepyrimidine. Yield: 32.1%.

Melting point (m.p.): 110°–111° C. Mass spectrum (m/e): 289 (M+), 233.

Example 65

2-(4-Benzylpiperazino)-4-amino-5,6-trimethylenepyrimidine (Compound No. 56)

A mixture of 0.45 g. of 2-(4-benzylpiperazino)-4-chloro-5,6-trimethylenepyrimidine, 10 ml. of ethanol and 7 ml. of 40% aqueous solution of methylamine was heated in a sealed tube at 100° C. for 8 hours. After the solvent was removed by distillation under reduced pressure, 2 N-hydrochloric acid and ethyl acetate were added to the resulting residue. The aqueous layer was separated and neutralized by adding 10% aqueous potassium carbonate and then extracted with ethyl acetate. The organic layer was separated and dried over magnesium sulfate. After the solvent was removed by distillation, the residue was purified by silica gel chromatography (5%-ethanol-chloroform) to give 0.41 g. of the hydrochloride of the desired product. Yield: 93%.

Melting point (m.p.): 195°–204° C. Mass spectrum (m/e): 323 (M+). IR spectrum ($cm^{-1}$): 1650, 1610, 1575.

We claim:

1. A compound selected from the group consisting of 2-piperazino-4-amino-5,6-tetramethylenepyrimidine; 2-[4-{3-(furan-2-yl)-acryloyl}piperazino]-4-amino-5,6-tetramethylenepyrimidine; 2-[4-(4-chlorophenyl)-piperazino]-4-amino-5,6-tetramethylenepyrimidine; 2-piperazino-4-methylamino-5,6-tetramethylenepyrimidine; 2-piperazino-4-dimethylamino-5,6-tetramethylenepyrimidine; 2-piperazino-4-morpholino-5,6-tetramethylenepyrimidine; 2-piperazino-4-amino-5,6-trimethylenepyrimidine; 2-(4-benzylpiperazino)-4-amino-5,6-trimethylenepyrimidine; and 2-piperazino-4-amino-5,6-pentamethylenepyrimidine.

2. The compound of claim 1 which is 2-piperazino-4-amino-5,6-tetramethylenepyrimidine.

3. The compound of claim 1 which is 2-[4-{3-(furan-2-yl)acryloyl}piperazino]-4-amino-5,6-tetramethylenepyrimidine.

4. The compound of claim 1 which is 2-[4-(4-chlorophenyl)-piperazino]-4-amino-5,6-tetramethylenepyrimidine.

5. The compound of claim 1 which is 2-piperazino-4-methylamino-5,6-tetramethylenepyrimidine.

6. The compound of claim 1 which is 2-piperazino-4-dimethylamino-5,6-tetramethylenepyrimidine.

7. The compound of claim 1 which is 2-piperazino-4-morpholino-5,6-tetramethylenepyrimidine.

8. The compound of claim 1 which is 2-piperazino-4-amino-5,6-trimethylenepyrimidine.

9. The compound of claim 1 which is 2-(4-benzyl-piperazino)-4-amino-5,6-trimethylenepyrimidine.

10. The compound of claim 1 which is 2-piperazino-4-amino-5,6-pentamethylenepyrimidine.

* * * * *